United States Patent
Kim et al.

(10) Patent No.: US 7,369,644 B2
(45) Date of Patent: May 6, 2008

(54) PRINTED CIRCUIT BOARD INSPECTION SYSTEM COMBINING X-RAY INSPECTION AND VISUAL INSPECTION

(75) Inventors: Jong-Won Kim, Yongin (KR); Dong-Hyun Lee, Seoul (KR); Seong-Cheol Hong, Suwon (KR)

(73) Assignee: Mirtec Co., Ltd. (KR)

( * ) Notice: Subject to any disclaimer, the term of this patent is extended or adjusted under 35 U.S.C. 154(b) by 84 days.

(21) Appl. No.: 10/576,229

(22) PCT Filed: Oct. 14, 2003

(86) PCT No.: PCT/KR03/02118

§ 371 (c)(1),
(2), (4) Date: Apr. 13, 2006

(87) PCT Pub. No.: WO2005/036148

PCT Pub. Date: Apr. 21, 2005

(65) Prior Publication Data

US 2007/0104315 A1    May 10, 2007

(51) Int. Cl.
*G01N 23/04* (2006.01)
(52) U.S. Cl. .................. 378/63; 378/57; 378/98.3
(58) Field of Classification Search .............. 378/57, 378/63, 98.3
See application file for complete search history.

(56) References Cited

U.S. PATENT DOCUMENTS

| | | | | |
|---|---|---|---|---|
| 4,542,290 A | * | 9/1985 | Tan et al. | 250/214 VT |
| 4,943,988 A | * | 7/1990 | Gerlach et al. | 378/108 |
| 5,590,170 A | * | 12/1996 | Zweig | 378/63 |
| 5,644,616 A | * | 7/1997 | Landi et al. | 378/206 |
| 6,272,204 B1 | | 8/2001 | Amtower et al. | 378/63 |
| 6,731,718 B2 | * | 5/2004 | Ogura et al. | 378/63 |
| 7,023,954 B2 | * | 4/2006 | Rafaeli et al. | 378/43 |
| 7,198,404 B2 | * | 4/2007 | Navab et al. | 378/206 |

FOREIGN PATENT DOCUMENTS

| | | |
|---|---|---|
| JP | 2-31144 | 2/1990 |
| JP | 10-253550 | 9/1998 |

(Continued)

OTHER PUBLICATIONS

PCT International Search Report; PCT/KR 03/02118; Dated: Dec. 3, 2003.

*Primary Examiner*—Edward J. Glick
*Assistant Examiner*—Thomas R. Artman
(74) *Attorney, Agent, or Firm*—Cantor Colburn LLP

(57) ABSTRACT

A circuit board inspection system combining an X-RAY inspection and a visual inspection comprises a transfer unit (3) that lands an inspected object (1) safely thereon and transfers the inspected object (1) to a predetermined position; a light generating unit (5) that is installed below the transfer unit (3) and emits a light having a predetermined wavelength to the inspected object (1); a light amplifying unit (7) that is installed on the opposite side of the light generating unit (5) to convert and amplify a predetermined light that transmits the inspected object (1) into a visible light; an optical unit (9) that optically illuminates the inspected object (1) to create a visual image; and a camera (11) that receives an X-ray image amplified through the light amplifying unit (7) or a visual image by the optical unit (9) to obtain information.

4 Claims, 1 Drawing Sheet

FOREIGN PATENT DOCUMENTS

| | | |
|---|---|---|
| JP | 11-295242 | 10/1999 |
| JP | 2000-352559 | 12/2000 |
| JP | 2002-168800 | 6/2002 |
| JP | 2003-106827 | 4/2003 |
| JP | 2003-269929 | 9/2003 |
| WO | WO 02/03045 A2 | 1/2002 |

* cited by examiner

US 7,369,644 B2

PRINTED CIRCUIT BOARD INSPECTION SYSTEM COMBINING X-RAY INSPECTION AND VISUAL INSPECTION

BACKGROUND OF THE INVENTION

1. Field of the Invention

The present invention relates to a circuit board inspection system combining an X-RAY inspection and a visual inspection and, more particularly, a circuit board inspection system combining an X-RAY inspection and a visual inspection that is implemented such that an X-RAY image formed by transmitting an X-RAY source and a visual image projected optically is processed with one camera, thereby attempting to simplify the system.

2. Description of the Related Art

Recently, as electronic devices have a tendency to be small, light and multi-functional, the integration degree of a printed circuit board and electronic components mounted thereon becomes rapidly improved. That is, the printed circuit board becomes multi-layered, and the patterns formed thereon become denser. Further, for the electronic components as well, since the integration degree becomes higher and he size becomes smaller, chances are grow much stronger that defects may occur unless much attention is paid in fabricating the printed circuit board or mounting the components on the printed circuit board. Therefore, in the process of fabricating the printed circuit board and mounting and soldering the components, a task that detects a defect generated during each unit process in an exact and timely manner becomes significantly needed.

Such an inspection system for inspecting the mounting state of components depends on characteristics of the components, which use typically an X-ray image, a video camera, and a laser, as a detection unit obtaining information on an inspected object.

The X-ray image represents an amplified light formed by emitting an X-ray beam illuminated from an X-ray source toward the inspected object, which is useful in detecting hidden defects of the inspected object.

The visual image is formed by capturing a visual frequency range of the inspected object, which is useful in detecting visual defects of the inspected object, such as insufficient solder (abnormal solder), missing (missing components), wrong insertion, misaligned components.

Therefore, recently, an inspection system integrating these two functions has been used.

The configuration is largely divided into an inspection system for obtaining information on the inspected object and a processing system for being inputted the obtained information and performing a predetermined processing to determine whether or not it has a defect The inspection system comprises a board holder that fixes the inspected object, a conveyer assembly that transfers the board holder to a predetermined position, an X-ray source that emits an X-ray toward the inspected object, an X-ray camera that obtains an X-ray image transmitting the inspected object, an optical camera that illuminates a light to the inspected object and obtains an optical image by a reflected light.

However, in the conventional inspection system as described above, since the X-ray camera and the optical camera are installed individually, the inspection system is complicated, and moreover, a manufacturing cost increases.

SUMMARY OF THE INVENTION

Thus, the present invention is devised to solve the above problem and an object of the present invention is to provide a circuit board inspection system combining an X-RAY inspection and a visual inspection by receiving information on an X-ray image and a visual image with one camera, thereby not only attempting to simplify the inspection system but also reducing a manufacturing cost.

To accomplish the above object, the present invention comprises a transfer unit that lands an inspected object safely thereon and transfers the inspected object to a predetermined position; a light generating unit that is installed below the transfer unit and emits a light having a predetermined wavelength to the inspected object; a light amplifying unit that is installed on the opposite side of the light generating unit to convert and amplify a predetermined light that transmits the inspected object into a visible light; an optical unit that optically illuminates the inspected object to create a visual image; and a camera that receives the X-ray image through the light amplifying unit or the visual image by the optical unit to obtain information.

The light amplifying unit and the light generating unit are placed vertically below the camera; the optical unit is placed laterally side by side with the light amplifying unit; on the light axis between the light generating unit and the camera, a half mirror is arranged with a predetermined angle; and, on the emitting light axis of the optical unit, a reflection mirror is arranged in a position being on the same line in a horizontal direction where the half mirror is placed.

The light generating unit is an X-ray source that emits an X-ray beam, and the camera is a CCD (Charged Couple Device) camera.

DETAILED DESCRIPTION OF THE PREFERRED EMBODIMENT

Figure 1:
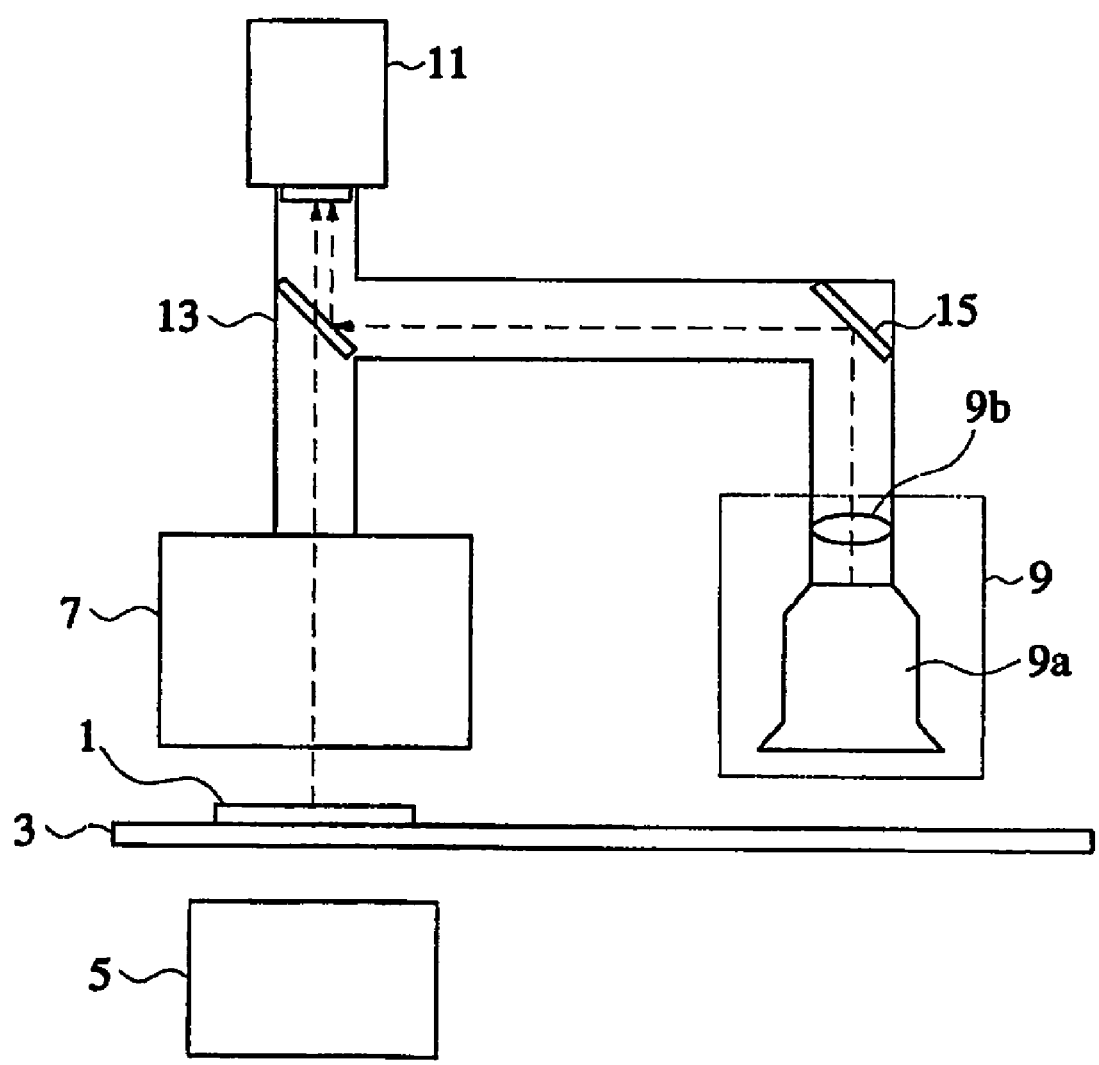
FIG. 1 is a schematic diagram illustrating a configuration of the inspection system combining an X-RAY inspection and a visual inspection according to an embodiment of the present invention.

A configuration and an operation of an embodiment of the present invention will be described below with reference to the accompanying drawing, FIG. 1.

As shown in FIG. 1, an embodiment of the present invention comprises a transfer unit 3 that lands an inspected object 1 safely thereon and transfers the inspected object to a predetermined direction; a light generating unit 5 that is installed below the transfer unit 3 and emits a light having a predetermined wavelength toward the inspected object 1; a light amplifying unit 7 that is installed on the opposite side of the light generating unit 5 to convert and amplify a predetermined light that transmits the inspected object 1 into a visible light; an optical unit 9 that optically illuminates the inspected object 1 to create a visual image; and a camera 11 that receives an X-ray image amplified through the light amplifying unit 7 or the visual image by the optical unit 9 to obtain an image. Preferably, the light generating unit 5 is an X-ray source that emits an X-ray beam, and the camera 11 is a CCD camera.

The light generating unit 5 is placed vertically below the camera 11 and the optical unit 9 is placed side by side with the light generating unit 5, and on the light axis between the light generating unit 5 and the camera 11, a half mirror 13 is installed slantly with a predetermined angle.

In addition, on the emitting light axis of the optical unit 9, a reflection mirror 15 is installed in a position being on the same line where the half mirror 13 is placed, maintaining the same angle with that of the tilted half mirror 13.

The optical unit 9 comprises an illuminator 9a for illuminating a light to the inspected object 1, and a lens 9b for adjusting a focus of the reflected light that is illuminated and reflected to the inspected object 9a.

As described above, since the present invention is implemented such that information on an X-ray image and a visual image is simultaneously obtained by using one camera, a simplification of the inspection system as well as a reduction of the manufacturing cost can also be obtained.

As above, while the invention has been described in terms of preferred embodiment, those of skilled in the art will recognize that the invention can be practiced with a variety of modification without departing from the scope of the present invention. Therefore, the scope of the present invention should be defined not by restricting to the illustrated embodiment, but by the appended claims as well as the equivalents thereof.

What is claimed is:

1. A circuit board inspection system combining an X-RAY inspection and a visual inspection, the inspection system comprising:
    a transfer unit that lands an inspected object safely thereon and transfers the inspected object to a predetermined position;
    a light generating unit that is installed below the transfer unit and emits a light having a predetermined wavelength to the inspected object;
    a light amplifying unit that is installed on the opposite side of the light generating unit to convert and amplify a predetermined light that transmits the inspected object into a visible light;
    an optical unit that optically illuminates the inspected object to create a visual image; and
    a camera that simultaneously receives an X-ray image amplified through the light amplifying unit and a visual image by the optical unit to obtain information,
    wherein, on a light axis between the light generating unit and the camera, a half mirror is arranged with a predetermined angle, and
    wherein, on an emitting light axis of the optical unit, a reflection mirror is arranged in a position being on a same line in a horizontal direction where the half mirror is placed.

2. The circuit board inspection system of claim 1,
    wherein the light amplifying unit and the light generating unit are placed vertically below the camera,
    wherein the optical unit is placed laterally side by side with the light amplifying unit.

3. The circuit board inspection system of claim 1, wherein the light generating unit is an X-ray source that emits an X-ray beam.

4. The circuit board inspection system of claim 1, wherein the camera is a CCD camera.

* * * * *